United States Patent [19]

Wall

[11] Patent Number: 4,693,722
[45] Date of Patent: * Sep. 15, 1987

[54] PROSTHETIC TEMPOROMANIBULAR CONDYLE UTILIZING A PROSTHETIC MENISCUS

[76] Inventor: William H. Wall, Suite 201 5139 Jimmy Carter Blvd., Atlanta, Ga. 30093

[*] Notice: The portion of the term of this patent subsequent to Mar. 5, 2002 has been disclaimed.

[21] Appl. No.: 699,138

[22] Filed: Feb. 7, 1985

Related U.S. Application Data

[63] Continuation-in-part of Ser. No. 524,474, Aug. 19, 1983, Pat. No. 4,502,161, which is a continuation of Ser. No. 303,826, Sep. 21, 1981, abandoned.

[51] Int. Cl.$^4$ .............................................. A61F 2/30
[52] U.S. Cl. ...................................................... 623/18
[58] Field of Search ............................ 623/16, 18, 11; 128/92 C, 92 R, 92 CA, 92 A, 92 YP; D24/33

[56] References Cited

U.S. PATENT DOCUMENTS 3,178,728  4/1965  Christensen .................... 128/92 C
3,900,025  8/1975  Barnes ............................ 128/92 YP
4,502,161  3/1985  Wall ................................ 128/92 C

OTHER PUBLICATIONS

Kent et al., "Temporomandibular Joint Condylar Prosthesis: A Ten Year Report," *Journal of Oral and Maxillofacial Surgery*, Apr. 1983, pp. 245-254.
Advertising material of VITEK, Inc. entitled: Vitek's New PROPLAST Stabilized TMJ Prosthetic Condyle: Geometrically Advanced Beyond its Clinically Proven Precurser.
Advertising material of VITEK, Inc. entitled: Now Vitek's PROPLAST Custom Glenoid Fossa Implant and the PROPLAST-stabilized TMJ, Condylar Prosthesis (Type VK)[1] Work Together as a Total TMJ Implant.
Advertising material of VITEK, Inc. entitled: Improve and Simplify a Variety of TMJ Restoration Procedures and Enhance Articulation.
Literature of VITEK, Inc. entitled PROPLAST Implant Material Sheeting and Laminates of Sheeting to TEFLON or Silicone Rubber, Copyright, Vitek, Inc., 1982, pp. 1-5.
Literature of VITEK, Inc. entitled: PROPLAST Temporomandibular Joint Condylar Prosthesis, Copyright, Vitek, Inc., 1982, pp. 1-7.

*Primary Examiner*—Richard J. Apley
*Assistant Examiner*—James Prizant
*Attorney, Agent, or Firm*—Eric P. Schellin

[57] ABSTRACT

A prosthetic device for a temporomandibular joint comprising a prosthetic condyle and a prosthetic meniscus. The prosthetic condyle conprises two plates that are clamped about the ramus of the mandible wherein one of the plates extends upwardly into a convex surface thereby forming the condyle. The prosthetic meniscus comprising a resilient insert which is inserted into the joint capsule and has a reinforcing mesh embedded therein, and an extension for attaching the meniscus to the temporal bone.

15 Claims, 9 Drawing Figures

PROSTHETIC TEMPOROMANIBULAR CONDYLE UTILIZING A PROSTHETIC MENISCUS

This application is a continuation-in-part application of U.S. patent application Ser. No. 524,474, filed Aug. 19, 1983, (now U.S. Pat. No. 4,502,161), which was a continuation of U.S. patent application Ser. No. 303,826, filed Sept. 21, 1981 which has since been abandoned.

BACKGROUND OF THE INVENTION

1. Field of the Invention:

The present invention is directed to a prosthetic device, and more specifically to a prosthetic substitute for the condyle of the mandible. A synthetic prosthetic meniscus is also used with the prosthetic condyle.

2. Description of the Prior Art:

The mandible or jaw bone is the largest and strongest bone in the face and provides a mounting structure for the teeth. The mandible consists of a horseshoe-shaped horizontal portion and two perpendicular portions called rami (ramus singular). Each ramus is provided with a condyloid process consisting of two portions the condyle and its supporting structure the neck. The condyle is located at the top of the ramus adjacent to the mandibular notch.

The condyle provides a surface for articulation with the articular meniscus of the temporo-mandibular joint. The top of the condyle consists of a convex portion that fits into the concave surface of the glenoid fossa of the temporal bone. The articular meniscus is located between these two surfaces. The condyle, articular meniscus and the mandibular fossa essentially act as a pivot point or hinge for the jaw as it moves up and down.

Due to accident or disease, the condyle may have to be replaced by a prosthetic device. Such a device is currently marketed by Vitek, Inc. of Houston, Texas. The Vitek prosthetic condyle is coated with Proplast, a material to encourage tissue ingrowth. Proplast is a registered trademark of Vitek, Inc. and is covered by U.S. Pat. Nos. 3,992,725 and 4,129,470. The underlying prosthetic itself is formed of a cast surgical cobalt-chromium-molybdenum alloy. The head and neck of the prosthetic are curved to facilitate placement.

The Vitek prosthetic condyle has been used in conjunction with a prosthetic glenoid fossa as disclosed in Kent et al, Temporomandibular Joint Condylar Prosthesis: A Ten Year Report, Journal of Oral and Maxillofacial Surgery, Vol. 41, Number 4, April 1983, pp. 245–254.

SUMMARY

The present invention comprises a prosthetic substitute for the condyle of the mandible which is used in conjunction with a prosthetic meniscus. First a condylectomy is performed to remove the damage condyle. The prosthetic condyle comprising two plates is then sandwiched around the ramus of a mandible below the condylectomy site. One of the plates extends upwardly past the condylectomy site and forms the prosthetic condyle having a convex surface. The other plate maybe provided with attachment tangs which engage apertures in the condyle plate. The second plate is also provided with threaded holes into the screws are secured after passing through the first plate and the ramus. Other embodiments of the prosthetic condyle are also disclosed.

A prosthetic meniscus disclosed in U.S. patent application Ser. No. 524,474, now U.S. Pat. No. 4,502,161, filed Aug. 19, 1983, discloses the synthetic meniscus used with the above described prosthetic condyle and as such is incorporated herein by reference. Briefly the meniscus comprises a resilient insert shaped to be received in the glenoid fossa and to provide a least substantially the same bearing surface as the natural meniscus. The insert is provided with reinforcing means which comprises a reinforcing mesh embedded in the insert and extending outside the insert to provide an extra-articular extension of reinforcing material. Portions of the reinforcing material can extend from the exterior of the insert within the joint for attachment of the insert to soft tissue which encapsulate the joint.

DETAILED DESCRIPTION

Figure 1:
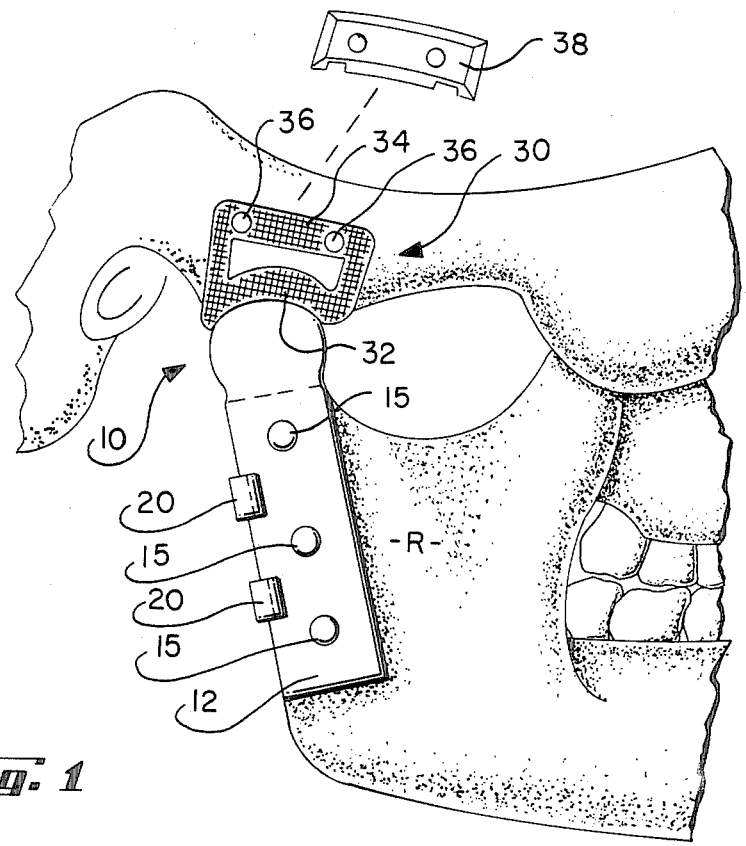
FIG. 1, is a perspective view of the subject prosthetic condyle with the prosthetic meniscus mounted in a patient.
Figure 2:
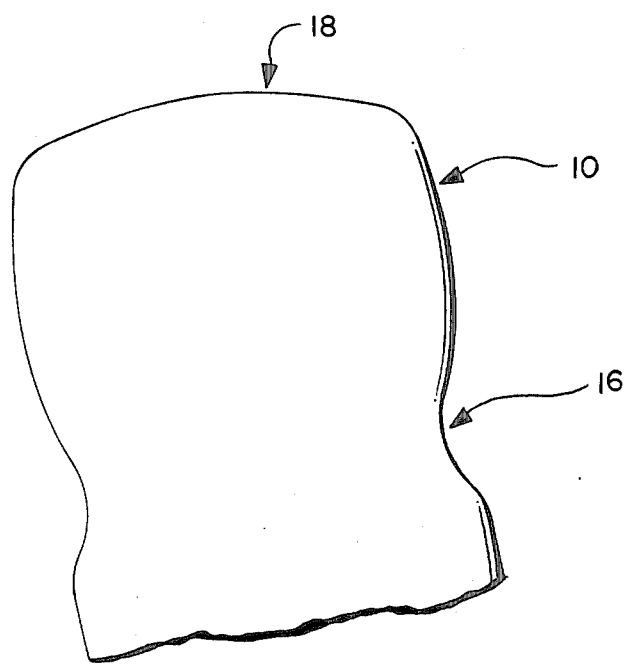
FIG. 2, is an enlarged view of the convex surface of the artifical condyle.
Figure 3:
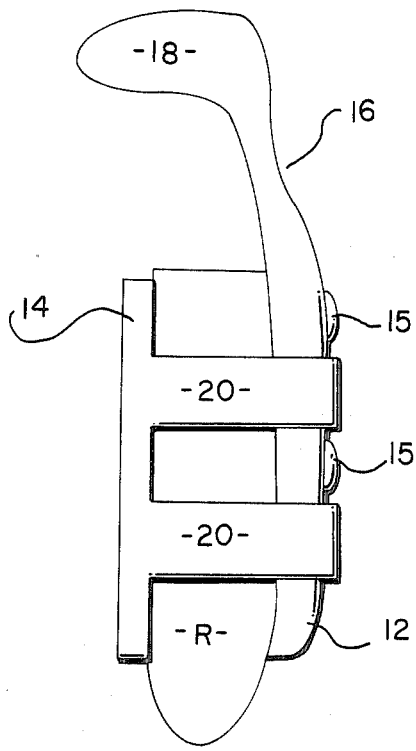
FIG. 3, is a rear view of the prosthetic condyle sandwiching the ramus of the mandible.

Prosthetic condyle 10 of the present invention, comprises two plates 12 and 14 which are sandwiched about ramus R. As illustrated in the figures, the natural condyle has been surgically removed. Screws 15 pass through plate 12, through the ramus, and are threaded into threaded holes 17 on plate 14, thereby forming a mounting means. Plate 12 is provided with an upwardly extending portion comprising nect portion 16 and convex portion 18. The convex portion essentially forms the convex surface of the natural condyle which is fitted into the concave glenoid fossa. Plate 14 however is shorter and forms a supporting plate for anchoring plate 12.

Plate 14 is also provided with J-shaped tangs 20 that extend around the outside edge of the ramus and key into receiving apertures 22 on plate 12. Apertures 22 comprises tang tip receiving means. As such the tangs provide for a more stable mounting of the prosthetic condyle than would be otherwise provided by only securing the plates with screws.

Figure 4:
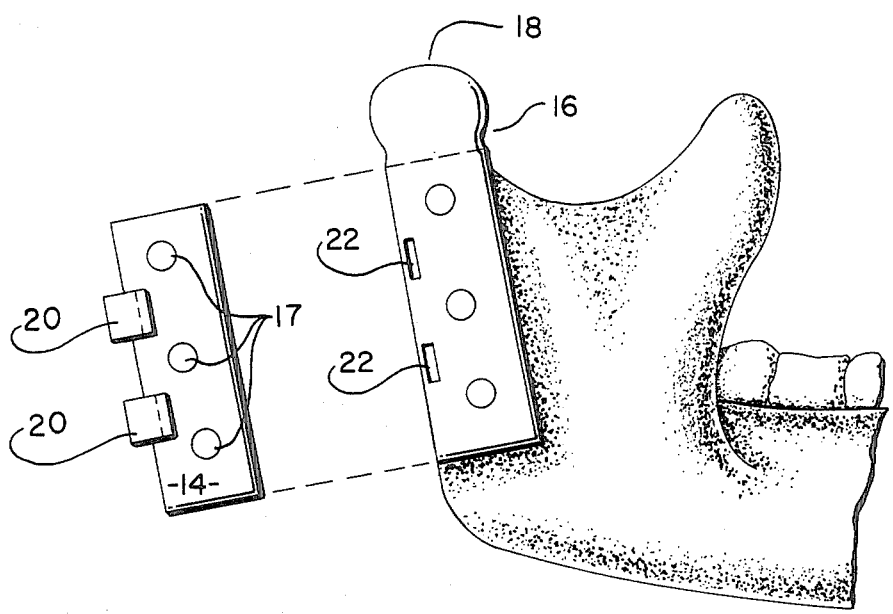
FIG. 4, is an exploded view of the subject prosthetic condyle.

The receiving apertures illustrated in FIG. 4, and the mating tips of the tangs are both rectangular. The apertures illustrated in the preferred embodiment are rectangular to facilitate manufacture of the device. However other polygonal shapes maybe provided as long as the tips of the tangs are able to mate with the apertures provided in the plate. For example, triangular apertures maybe used with triangular tang tips.

As illustrated in FIG. 1, the present prosthetic condyle is used together with a prosthetic meniscus 30 disclosed in the parent application. In that the prosthetic meniscus was adequately disclosed in that application, which is incorporated herein by reference, the meniscus will not be discussed in greater detail except as it used together with the subject prosthetic condyle.

Prosthetic meniscus 30 includes body portion 32 which is constructed of a resilient material and an integrally formed U-shaped or broad strut 34 which extends outside the joint. Strut 34 includes at least two openings 36 therein for attachment of meniscus 30 to the temporal bone. Embedded in the body and strut is a mesh of reinforcing material of the type described in the referenced application. The shape of the body portion conforms to the shape of the natural meniscus of the temporomandibular joint. The body portion of the meniscus lies between the prosthetic condyle and the glenoid fossa of the temporal bome. A stainless steel cover 38 is provided for protection, and attachment of the strut.

Figure 5:
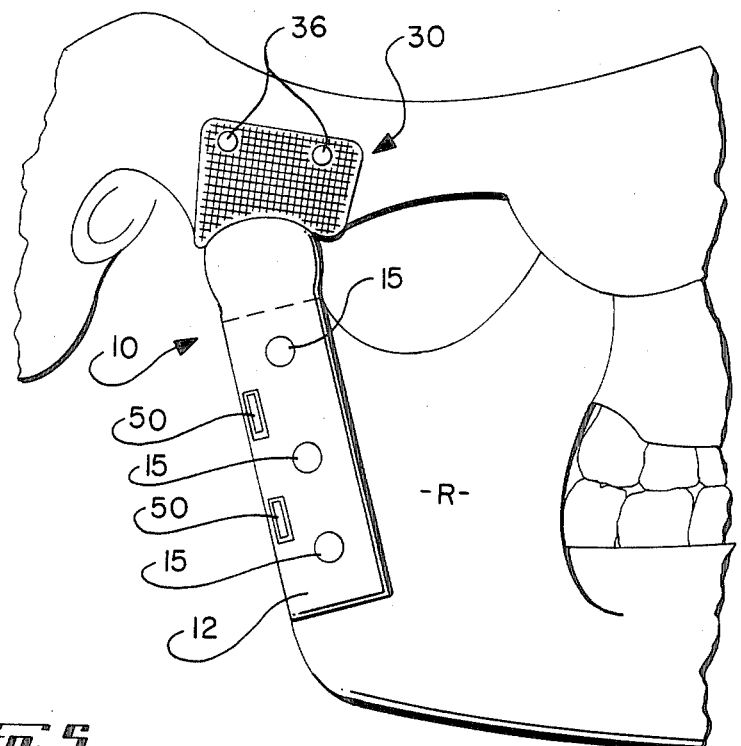
FIG. 5, is a perspective view of another embodiment of the prosthetic condyle and meniscus.

As illustrated in FIG. 5, meniscus 30 can also be formed without the opening created by the U-shaped strut 34, and also provided with more openings. This construction results in a stronger but somewhat less flexible connection between the body and the extension. Please note however, that either of the discussed prosthetic meniscus embodiments can be used with any of the disclosed prosthetic condyles.

Figure 6:
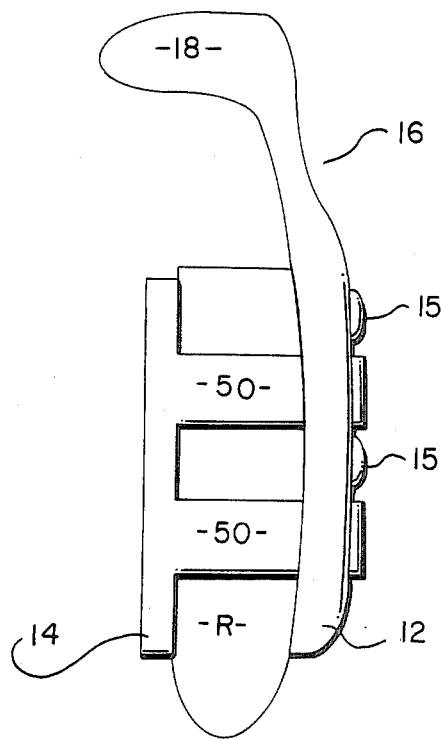
FIG. 6, is a rear view of the embodiment illustrated in FIG. 5.
Figure 7:
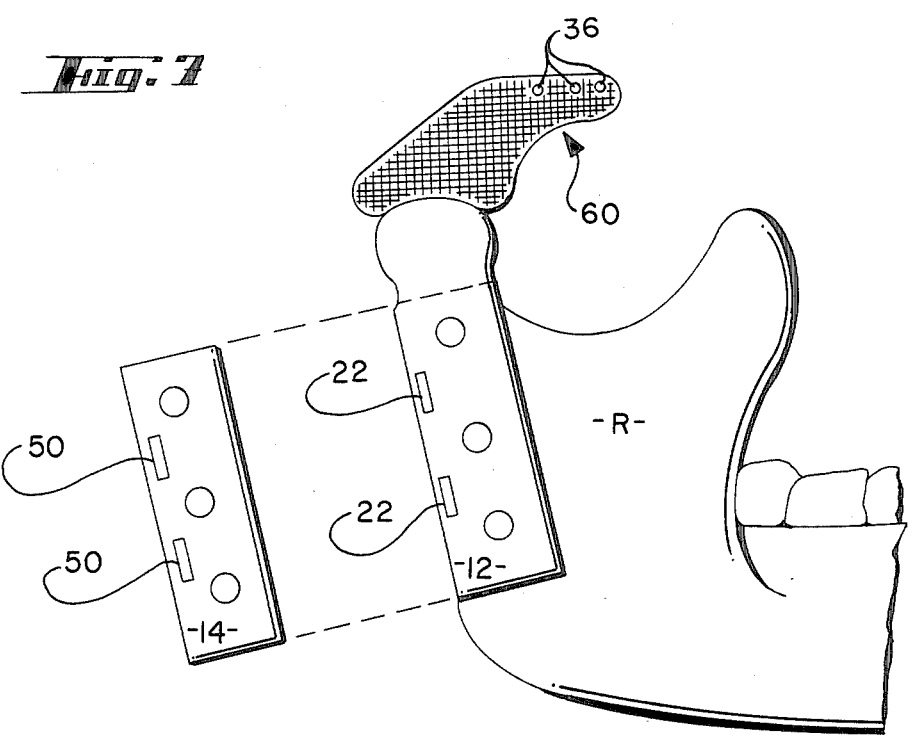
FIG. 7, is an exploded view of the embodiment illustrated in FIG. 5 provided with another embodiment of the prosthetic meniscus.

The alternative condyle embodiment illustrated in FIGS. 5, 6 and 7, is very similar to the previously discussed prosthetic condyle except for the configuration of tange 50. As with the previous embodiment plates 12 and 14 are fastened together, so as to sandwich the ramus therebetween. The plates are secured by screws 15 that pass through plate 12 and the ramus and are threaded into apertures in plate 14.

In this embodiment the tangs are not J-shaped but are straight projections that extend directly into receiving apertures 22 on plate 12. In that the tangs extend directly to plate 12 and not around the rear edge of the ramus; grooves or channels may have to be cut in the ramus to accomodate the tangs. As with the previous embodiment the tang tips mate in apertures 22 of plate 12 and therefore the cross section of the tang tips must conform with the shape of the receiving apertures.

FIG. 7 also illustrates an alternate embodiment of the prosthetic meniscus. The illustrated meniscus is provided with a zygomatic mounting portion 60 having holes 36. This mounting portion is directly fastened to the zygomatic arch of the temporal bone by screws passing through holes 36. A similar prosthetic meniscus is marketed by Vitek, Inc. of Houston, Texas.

Figure 8:
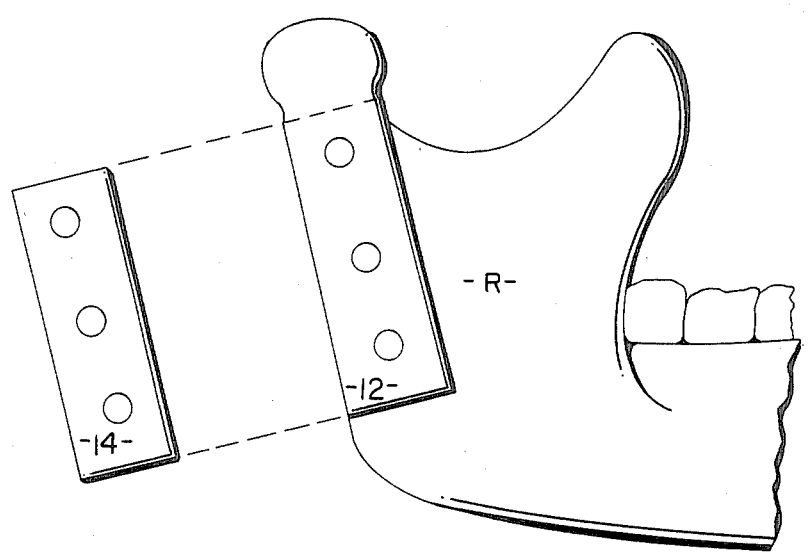
FIG. 8, is an exploded view of another embodiment of the prosthetic condyle.

The prosthetic condyle illustrated in FIG. 8 is a more simplified device than the previously discussed prosthetic condyles. More specifically plate 14 is not provided with tangs that mate in receiving apertures in plate 12. Instead only screws are used to mount the plates to the ramus similar to the previous embodiments.

Figure 9:
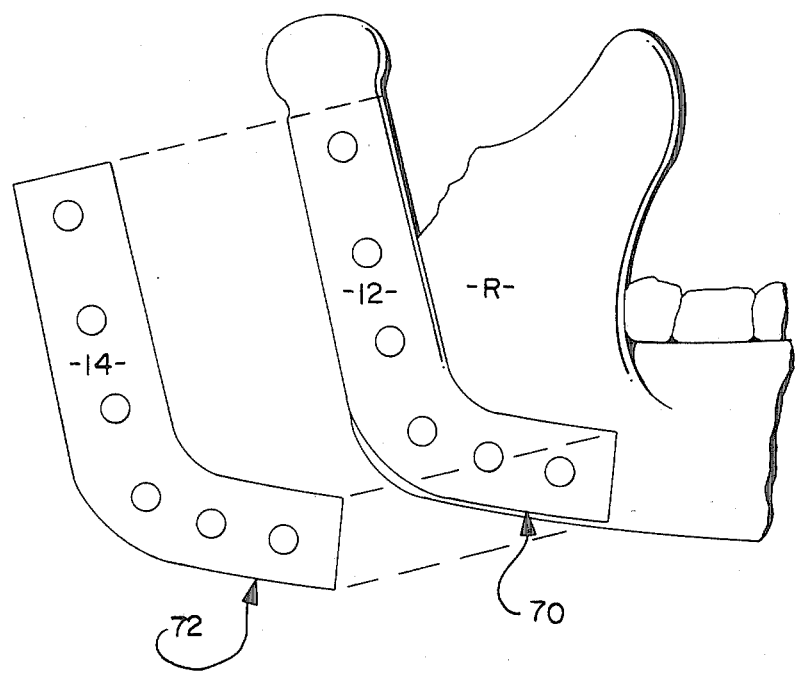
FIG. 9 is an exploded view of another embodiment of the prosthetic condyle.

The prosthetic condyle illustrated in FIG. 9, is designed to be used where the condyle is severely damaged and the ramus is also damaged and unable to support one of the above described embodiments. Plates 12 and 14 are provided with curved extensions 70 and 72, respectively. The curved extensions sandwich and horizontal portion of the mandible therebetween so as to provide a secure mounting. As with the previously discussed embodiments screws pass through extension 70 and the obstructing bone, and are threaded into apertures in extension 72. Tangs may also be provided along the periphery of plate 14 and extension 72 which mate in receiving apertures in plate 12 and extension 70, to provide a more stable prosthetic condyle.

The flat portions of the mounting plates and the prosthetic meniscus itself maybe coated with a material to encourage the ingrowth of tissue, such as Proplast. This coating encourages blood flow through adjacent tissue while also eliminating voids between the implant and adjacent tissues.

The above prosthetic device has been described with regards to the attached figures, but should not be so limited but should be limited solely by the claims that follow.

I claim:

1. A prosthetic apparatus for the temporomandibular joint, comprising:
   a prosthetic condyle comprising first and second plates that are adapted to be mounted to opposite sides of the ramus of the mandible;
   a prosthetic meniscus which is adapted to be inserted into the temporomandibular joint capsule between the temporal bone of the patient and the prosthetic condyle, the prosthetic meniscus comprises a resilient insert shaped to be received in the joint capsule positioned adjacent to the glenoid fossa and defining an extension thereof extending outside the joint capsule, reinforcing mesh is embedded within the resilient insert and integrally extends into the extension, and means for fixedly attaching the extending end of the extension to an outer bone surface of the temporal bone outside of the joint capsule, the extension being connected to the insert so as the permit relative movement between the insert and the extension; wherein said first plate of the prosthetic condyle is provided with a convex surface that is located directly adjacent to the prosthetic meniscus.
   said second and first plates comprising a flat portion, wherein the flat portion of the first plate is adapted to be mounted to the ramus of the mandible and said first plate also comprises a curved neck portion that extends from the flat portion and on which a convex portion is provided; wherein the flat portion of the first plate further comprises at least one polygonal aperture and, the flat protion of the second plate comprises at least one tang having a polygonal tip that is adapted to mate with with polygonal aperture in the first plate.

2. A prosthetic apparatus as defined by claim 1 wherein the prosthetic meniscus comprises a U-shaped strut that is provided with the extension.

3. A prosthetic apparatus as defined by claim wherein the second plate comprises a flat portion having threaded apertures, the flat portion of the first plate is also provided with round apertures that are positioned directly across from the apertures in the second plate.

4. A prosthetic apparatus as defined by claim wherein the flat portion of the first and second plates is coated with a material for encouraging the ingrowth of tissue.

5. A prosthetic apparatus as defined by claim 1 wherein the prosthetic meniscus is provided with a zygomatic mounting portion, which comprises the extension for securing the prosthetic meniscus to a zygomatic arch of a patient.

6. A prosthetic apparatus as defined by claim 1 in the prosthetic meniscus is coated with a material to encourage the ingrowth of tissue.

7. A prosthetic apparatus as defined by claim 4 further comprising screws that are inserted through the round apertures in the first plate and threaded onto the threaded apertures of the second plate.

8. A prosthetic apparatus as defined by claim 7 wherein the first and second plates are provided with curved extensions that are adapted to be secured to a horizontal portion of a mandible.

9. A prosthetic apparatus as defined by claim 7 wherein at least one tang is J-shaped so that it is adaptable to fit around the back of a ramus.

10. A prosthetic condyle for the temporomandibular joint, comprising:
a first plate provided with a convex surface and tang receiving means;
a second plate having at least one tang extending from the plate and which is adapted to engage the tang receiving means on the first plate; and
mounting means whereby the first and second plates are adapted to be mounted on opposite sides of the ramus of the mandible thereby providing the convex surface as the prosthetic condyle.

11. A prosthetic condyle as defined by claim 10 wherein at least one tang is provided with a polygonal tip and the tang receiving means comprises at least one polygonal aperture into which the polygonal tip of the tang is inserted.

12. A prosthetic condyle as defined by claim 11, wherein the mounting means comprises round apertures in the first plate and threaded apertures in second plate that are adapted to receive mounting screws.

13. A prosthetic condyle as defined by claim 12 wherein the first and second plates are provided with flat portions that are coated with a material to encourage the ingrowth of tissue.

14. A prosthetic condyle as defined by claim wherein the first and second plates are provided with curved extensions that are adapted to be secured to a horizontal portion of a mandible.

15. A prosthetic condyle as defined by claim 13 wherein at least one tang is J-shaped.

* * * * *